United States Patent [19]

Sasaki et al.

[11] Patent Number: 5,016,975
[45] Date of Patent: May 21, 1991

[54] ELECTRONIC ENDOSCOPE PROVIDED WITH A SAMPLE-HOLD CIRCUIT

[75] Inventors: Masahiko Sasaki; Tadashi Kato; Hiroyoshi Fujimori, all of Hachioji; Tatsuo Nagasaki, Musashino; Fumiyuki Onoda, Tokyo; Toshiaki Nishikori, Sagamihara; Hideo Tomabechi, Higashiyamato; Kazutake Sugawara; Kazuo Nakamura, both of Hachioji; Ootaro Ando; Koichi Karaki, both of Hino, all of Japan

[73] Assignee: Olympus Optical Co., Ltd., Tokyo, Japan

[21] Appl. No.: 364,504

[22] Filed: Jun. 8, 1989

Related U.S. Application Data

[63] Continuation of Ser. No. 760,427, Jul. 30, 1985, abandoned.

[30] Foreign Application Priority Data

Jul. 31, 1984 [JP] Japan .............................. 59-162523
Aug. 21, 1984 [JP] Japan .............................. 59-173832
Jan. 31, 1985 [JP] Japan .............................. 60-16910
May 28, 1985 [JP] Japan .............................. 60-114829

[51] Int. Cl.$^5$ ............................................ G02B 23/26
[52] U.S. Cl. .................................. 350/96.26; 362/279
[58] Field of Search ............... 350/96.24, 96.25, 96.26; 362/279; 128/6, 303.15; 358/48, 161, 168, 901

[56] References Cited

U.S. PATENT DOCUMENTS

| | | | |
|---|---|---|---|
| 1,335,889 | 4/1920 | Fulton | 362/279 |
| 1,467,194 | 9/1923 | Petersen | 362/279 |
| 1,659,409 | 2/1928 | Porter | 362/279 |
| 1,703,668 | 2/1929 | Grosius | 362/279 |

Primary Examiner—William L. Sikes
Assistant Examiner—Robert E. Wise
Attorney, Agent, or Firm—Armstrong, Nikaido, Marmelstein, Kubovcik, & Murray

[57] ABSTRACT

An electronic endoscope having a light emitting unit for emitting illuminating light from the tip of the insertable part, a solid state imaging device at the tip for receiving an illuminated light image, a sample-holding circuit for sample-holding an output signal from the solid state imaging device, a light source for such light emitting unit and an iris device in such light source, the iris device comprising a diaphragm device for preventing the spectral characteristics of the endoscope from being changed due to the amount of light reduction which consists of a diaphragm assembly consisting of two dimensionally diaphragm units which consists of light passing openings with small sectional area and light shading parts formed by tubular surfaces surrounding the side surfaces of the openings, positioned in the beam emitted from illuminating lamp, and provided with means for turning diaphragm assembly from a position where the tubular surfaces are in parallel with the axis of the illumination beam to a position where the axes are at an angle.

12 Claims, 14 Drawing Sheets

FLUX OF LIGHT

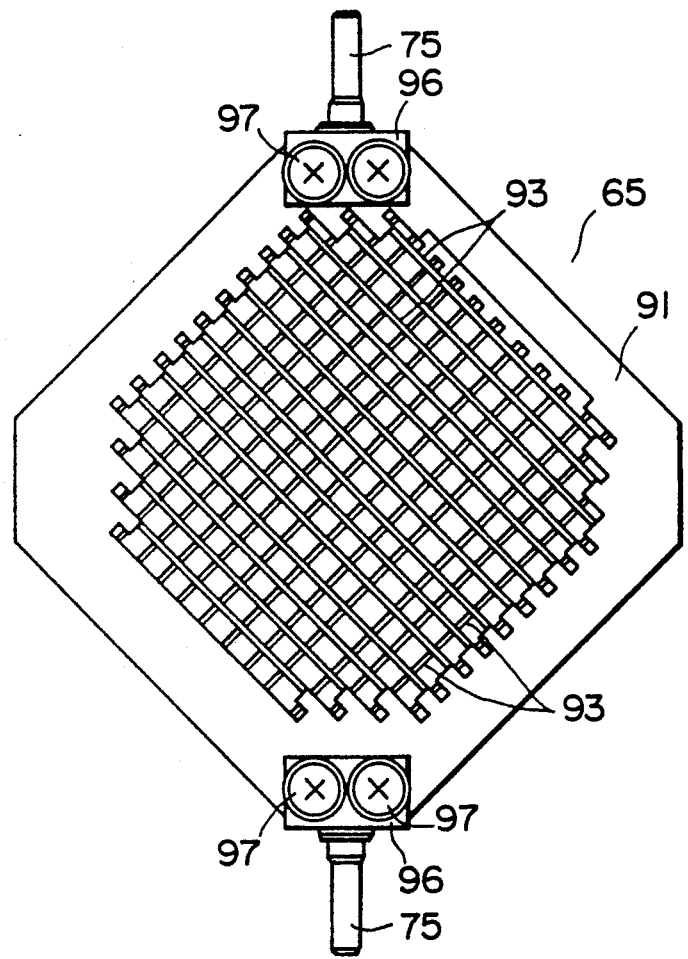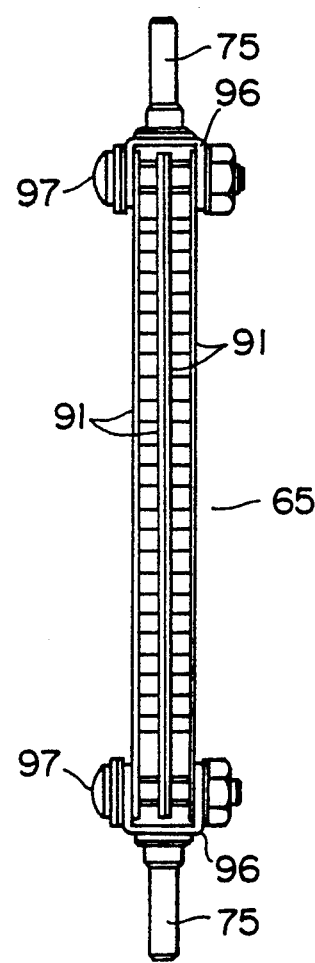

FIG.27
FIG.28
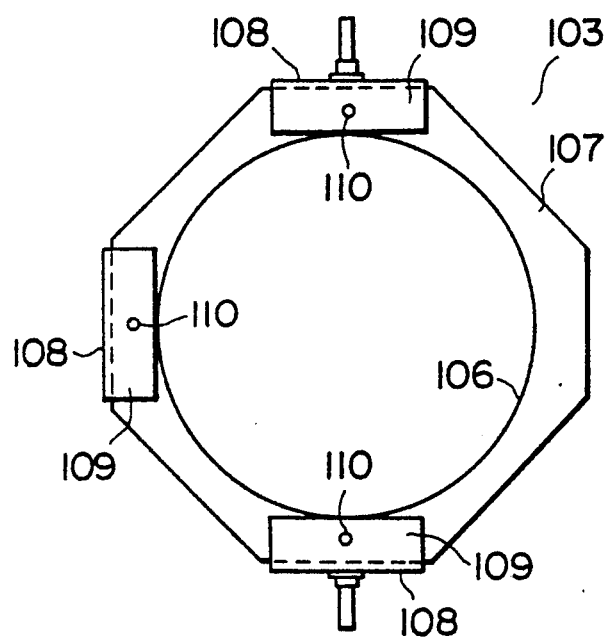
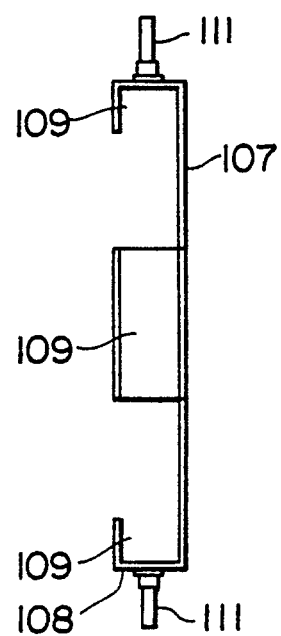
FIG.29
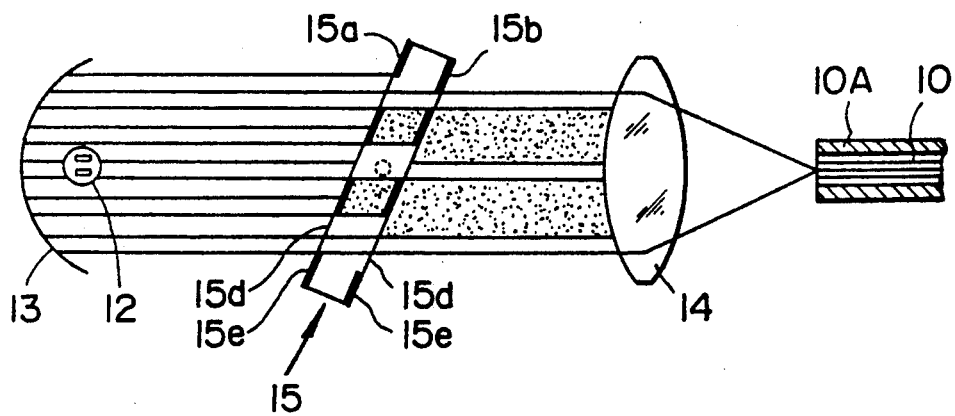

ELECTRONIC ENDOSCOPE PROVIDED WITH A SAMPLE-HOLD CIRCUIT

This application is a continuation of application Ser. No. 760,427 filed July 30, 1985, now abandoned.

FIELD OF THE INVENTION AND RELATED ART STATEMENT

The invention relates to an electronic endoscope having a sample-hold circuit and to a diaphragm device for a light source in such endoscope for preventing the spectral characteristics, etc. of the light from being changed by the amount of reduction.

Recent years have seen practical use of some endoscopes which make it possible to display a picture image of a subject on a display device, such as Braun tube using a solid state image pick-up device.

In comparison with endoscopes which form optical images on the image guide fibers, an electronic endoscope using such a solid state image pick-up device has the advantages that it is easier to record the picture image. The endoscope can be made smaller and smaller in size as high integration technology progress.

An endoscope using solid state image pick-up device, however, has problems wherein, if the quantity of light incident on the light receiving element on the imaging surface is too much, excessive charges leak to the periphery and a blooming phenomenon occurs on the reproducing screen. This, thereby, makes it impossible to reproduce the image of that portion faithfully and the image pick-up is made impossible until the normal state is restored.

For this reason, it is more necessary for an electronic endoscope than for an endoscope using image guide fibers to ably adjust the quantity of illuminating light to a proper level.

A diaphragm device is disclosed in the Japanese Utility Model Journal No. 53-108239 and has a hollow cylindrical diaphragm body with two openings provided in its wall surface symmetrically interposing the center axis of the hollow cylinder. These two openings are arranged so that the line connecting the centers of the openings comes into agreement with the optical axis of the beam when the openings permit most of the beam to pass. When this diaphragm body is turned, the overlap of the openings is changed, thereby changing the quantity of light to be passed.

This prior art has the disadvantage that the more the opening is reduced, the narrower the width of the passing beam becomes. The incident range on the incident end surface of the light guide made of an optical fiber bundle becomes narrower. Also the angle of incidence becomes smaller and the illuminating angle also becomes smaller accordingly.

For this reason, as the amount of reduction increases, the periphery of the visual field becomes dark.

Another prior art known is the diaphragm device shown in FIG. 1.

This is, in an optical system which is shown, the light from an electric discharge lamp 121 as a light source is reflected by a concave reflecting mirror 122 and is made into an approximately parallel beam. The parallel beam is then condensed by the condenser 123 and irradiated onto the light inlet end of the light guide fibers as illumination light transfer means. A disc diaphragm 125 with a fan-shaped cut as shown in FIG. 2 is arranged on the optical path between the condenser 123 and light guide fibers 124. By moving this diaphragm 125 (downward in FIG. 2), part of the beam is shielded in accordance with the amount of movement to change the quantity of light incident on the light guide fibers 124, thereby adjusting the quantity of the illuminating light to be fired from the other end of the light guide fibers 124.

In this prior art device, however, as the reduction is made by the diaphragm 125, the beam is shielded from the periphery. Therefore, the illumination light quantity distribution characteristics with regard to the angle of the illuminating light fired from the end surface of the light guide fibers 124 to the subject, i.e. the light distribution characteristics, are changed. Also, since the light guide fibers 124 have a different number of openings depending on the wavelength, the spectral characteristics are also changed when the light is shielded from peripheral side. For this reason, the color tone of the subject is changed depending on the amount of reduction. There is a fear of erroneous diagnosis and this poses a big problem for the endoscope used for diagnosis. Further, this shape results in a delay in response speed of the diaphragm and is not suitable for automatic light adjustment.

OBJECT AND SUMMARY OF THE INVENTION

An object of this invention is to provide an electronic endoscope with a sample-hold circuit and a light source device for such endoscope in which the spectral characteristics are not changed by the amount of reduction.

Another object of this invention is to provide a diaphragm device of the light source device for such an electronic endoscope which can prevent blooming.

A further object of this invention is to provide a diaphragm device of the light source for such an electronic endoscope which can automatically set the quantity of the illuminating light suitable for observation.

This invention forms a diaphragm consisting of many short pipe-like diaphragm units with the side surfaces used as a light shielding portion and with an opening of small area inside, wherein by inclining the diaphragm, the quantity of the passing light per unit area can be approximately uniformly changed.

BRIEF DESCRIPTION OF THE DRAWINGS

The invention will be better understood from the following description, taken with the appended drawings, in which

FIG. 8 is a block diagram for illustrating another endoscope equipped with;

FIG. 14 is a front view of the diaphragm and monitoring assembly of FIG. 10;

FIG. 15 is a side view of the diaphragm and monitoring assembly of FIG. 10;

FIG. 27 is a front view of a holding frame for the diaphragm of FIG. 24;

FIG. 28 is a side view of the holding frame of FIG. 27;

FIG. 29 is an explanatory drawing showing the diaphragm device of a further embodiment of the present invention;

DETAILED DESCRIPTION OF PREFERRED EMBODIMENTS

Figure 1:
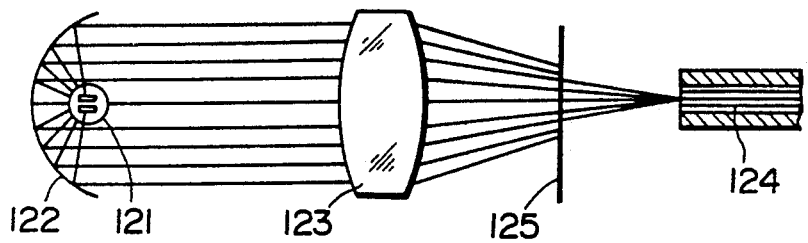
FIG. 1 is an explanatory drawing showing an optical system of a diaphragm of the prior art.
Figure 2:
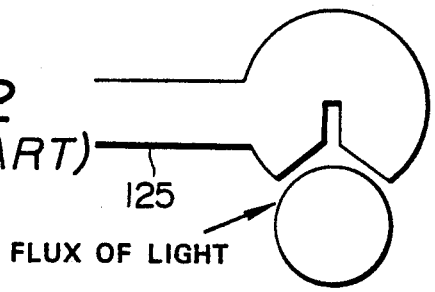
FIG. 2 is a front view showing the shape of said diaphragm device.
Figure 3:
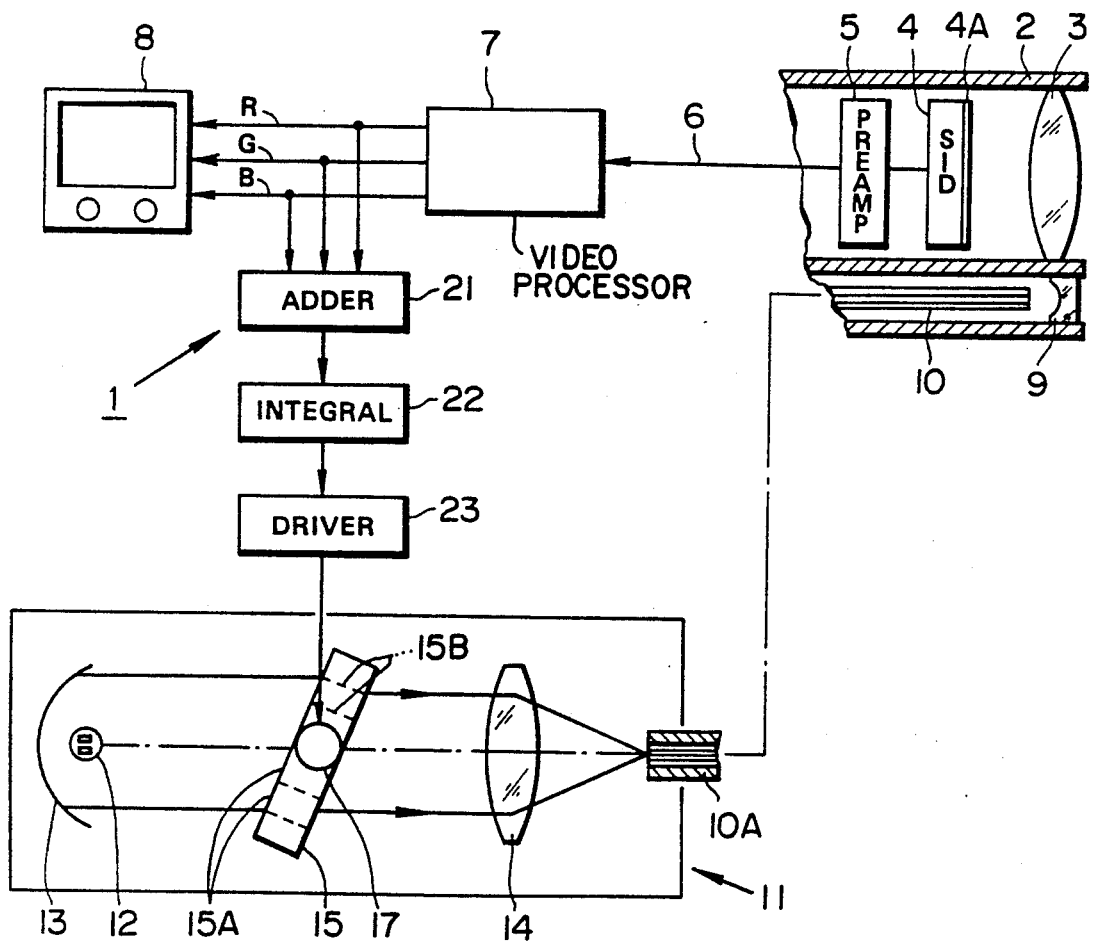
FIG. 3 is a block diagram of an electronic endoscope equipped with a video processor.

As shown in FIG. 3, the endoscope 1 equipped with the video processor has an object lens 3 for image forming at the end of a narrow inserted part of the endoscope and a solid state image pick-up device 4 such a CCD (Charge Coupled Device) located at such a place that its imaging surface is positioned at the image forming position of the object lens 3. On the imaging surface of the solid state image pick-up device 4, light receiving elements with photoelectric conversion function are regularly arranged. Immediately before the imaging surface a mosaic-arranged three primary color filter 4A which transmits only the light of each wavelength of the three primary colors is installed. In accordance with the clock signals applied to the solid state image pick-up device 4, the signals corresponding to the picture elements passed through the red, green and blue transmission filters are sequentially output. These signals are amplified by a preamplifier 5 with low noise factor, passed through the signal cable 6, separated into the color signals R, G and B, and taken in by a sample hold circuit in the video processor 7. After they are amplified, periodic signals are superimposed on them which are then input to a color television receiver 8 for monitoring and displaying as a color picture.

In the aforementioned inserted part 2, a light distributing lens 9 is provided adjacent to the object lens 3 and a light guide 10 consisting of flexible fiber bundle is inserted in such a way that its light outlet end faces the inside of the light distributing lens 9.

The rear end of the light guide 10 can be detachably connected to a light source device 11 equipped through a connector 10A.

To the rear end of the light guide 10, that is, the light inlet end, the light of an illuminating lamp 12 such as discharge lamp reflected by a concave parabolic reflecting mirror 13, made into approximately parallel beam and condensed by a condenser 14 is irradiated.

The quantity of the illuminating light made into approximately parallel beam by the reflecting mirror 13 and irradiated onto the inlet end of the light guide can be changed by means of a diaphragm 15 arranged in the optical path between the reflecting mirror 13 and condenser 14, for example, at the pupil position of the condenser 14.

Figure 5:
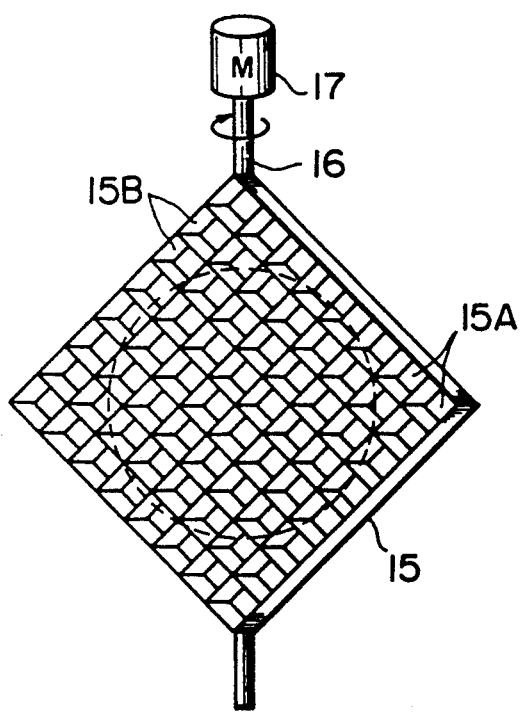
FIG. 5 is a perspective view showing the diaphragm device of FIG. 4 with a rotating unit

As shown in FIG. 5, the diaphragm 15 is made by assembling narrow belt-like metal plates lengthwise and crosswise into a square shape, thus making a frame having small square grids. The rectangular parallel piped portion inside each grid becomes an opening 15A which passes the light and the outer peripheral frame of each opening 15A, i.e. the square metal plate portion which form a short square pipe becomes a light shading portion 15B. In other words, each opening 15A and the surrounding light shading portion 15B form a small diaphragm unit. A plurality of such diaphragm units are arranged two-dimensionally to form the diaphragm 15. The diaphragm units are so arranged that the center axes of the openings 15A are in parallel with one another. In other words, the frame faces of the light shading portions 15B are in parallel with a single axis.

As shown in FIG. 5, the aforementioned diaphragm 15 is provided with shafts 16 which are supported by bearings (not illustrated) so that it can turn around the straight line diagonally connecting two edges of the square plate with appropriate thickness (or short square pillar). One of the shafts 16 is connected to the rotating shaft of a motor 17 as a driving means. This diaphragm 15 and motor 17 form the diaphragm device.

The light shading 15B of the diaphragm 15 can be directly air-cooled and is constructed to be heat-resistant. The circle shown in a broken line in FIG. 5 shows the range of the parallel beam in the optical path in which the diaphragm 15 is arranged. The diaphragm has enough area to cover the extended area of the parallel beam (even when inclined).

Figure 4:
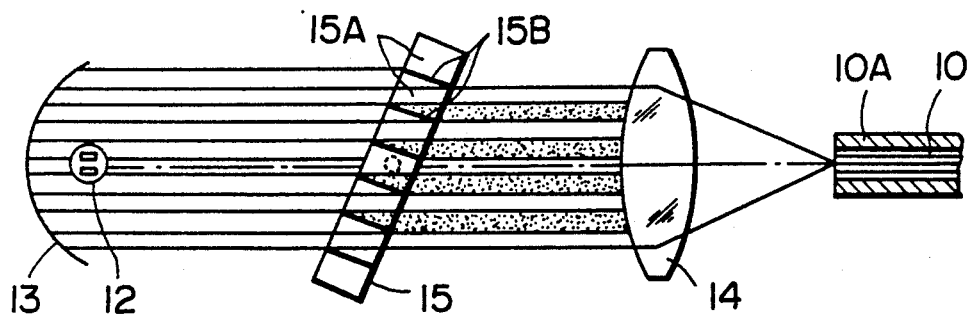
FIG. 4 is a sectional view showing the optical system portion of a light source device for use with the endoscope of FIG. 3 and with the electronic endoscope with a sample-hold circuit of the instant invention illustrated in FIG. 9.

If the diaphragm 15 is turned and inclined as shown in FIG. 4 from its normal state, i.e. the state in which the plate surface is at right angles to the optical axis, in other words, the state in which each face of each light shading portion 15B is parallel with the optical axis, the light hitting the light shading portions 15B is interrupted. The quantity of the light to be sent toward the condenser 14 is approximately uniformly reduced by the diaphragm units (the light incident on the diaphragm is shielded by the light shading portions 15B, the quantity of the light after passing through the diaphragm 15 is reduced, as shown by aventurine-shaped in FIG. 4).

The rotating angle of the diaphragm 15 can be automatically adjusted on basis of the imaging signal.

The color signals R, G and B, output from the video processor 7, are processed in the adder 21 to form luminance signal components which are then integrated by an integrating circuit in integral 22 to make the dimmer signals of reduction control signal which is then applied to the motor driving circuit 23.

The adder 21 makes the dimmer signal by holding the color balance. The integrating circuit 22 corresponds to the light receiving period of the signal output from each light receiving element and is set at the integral time constant of more than about 1 frame. In accordance with the size of the integrated signal level, the rotating angle of motor 17 is controlled. If the level of the dimmer signal passing through the integrating circuit 22 is high, the driving voltage increases, and the rotating angle to rotate the shaft of motor 17 against the force of, for example, a coil spring, is increased. That is, as the level of the dimmer signal becomes high, the rotating angle increases. Therefore, the quantity of the light passing through the diaphragm 15 is decreased.

If the diaphragm 15 is inclined, the center axes of the openings 15A are inclined against the optical axis and the quantity of the light hit and shielded by the square pipe-like light shading 15B at the periphery of the openings 15A is increased, thereby reducing the quantity of light. Since the quantity of light is approximately uniformly reduced by the square grid-like diaphragm units, the entire beam is approximately uniformly reduced. Therefore, the relative intensity distribution with regard to the angle of incidence of light irradiated to the inlet end of the light guide 10 is hardly changed from the state of no reduction and the light distributing characteristic of the light irradiated from the outlet end of the light guide 10 to the subject is not changed and the spectral characteristic is also not changed.

When the endoscope 1, is placed near to a subject, such as, affected part, to observe detail or placed away from the subject for general characteristics, the quantity of light reflected from the subject changes, depending on the distance. Therefore, the optimum luminous intensity changes. The signals, corresponding to the picture elements output, from the solid state image pick-up device 4 are taken in and displayed in color on the color television set 8. Also, the separated color signals R, G and B are added and further integrated by the integrating circuits 24 and, in accordance with the level of the dimmer signal, which reflects the quantity of the incoming light reflected from the subject during 1-frame period, the rotating angle of the motor 17, or diaphragm 15, is changed. For example, if the quantity of incoming light is too big, the level of the dimmer signal becomes high and the diaphragm is turned to a large angle, thus increasing the quantity of shielded light. After the 1-frame period, the luminous intensity is set at a proper level. If the quantity of the incoming light is too small, the level of the dimmer signal becomes low and the diaphragm 15 is maintained in an almost opened state (almost no rotation). This means not only that the blooming phenomenon can be prevented but, also, that the luminous intensity is always automatically adjusted to a level suitable for imaging.

Therefore, the operator is released from making adjustments each time the distance to a subject, or the intensity of the reflected light, changes and can devote himself to the diagnosis or medical treatment. This results in accurate diagnosis and proper medical treatment.

A diaphragm device, with quick response, can be realized because only a small rotation of the diaphragm immediately changes the quantity of light. Also, since the light distributing characteristic does not change even if the diaphragm is moved in the closing direction from the opened state, it is possible to realize illumination for color imaging with good color reproducibility at any diaphragm position.

Figure 6:
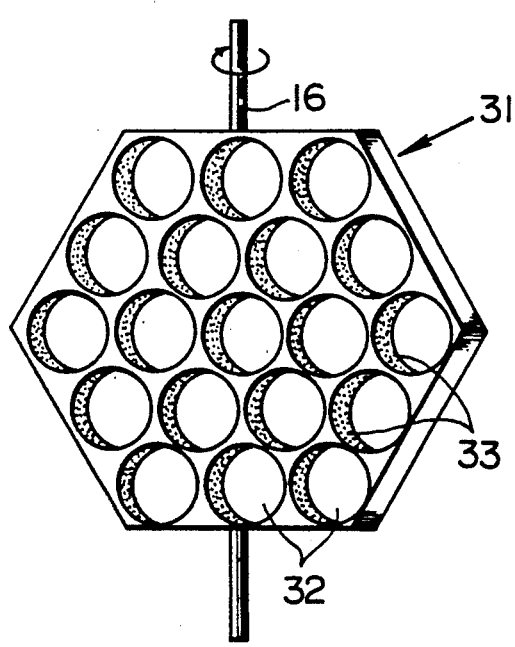
FIG. 6 is a perspective view showing and diaphragm for use with the endoscope of FIG. 5 and the electronic endoscope with a sample-hold circuit of the instant invention.
Figure 7A:
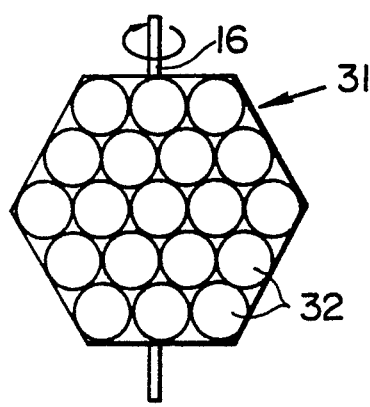
FIG. 7 (a) is a front view showing the diaphragm opened and FIG. 7 (b) is a perspective view showing the diaphragm closed.
Figure 7B:
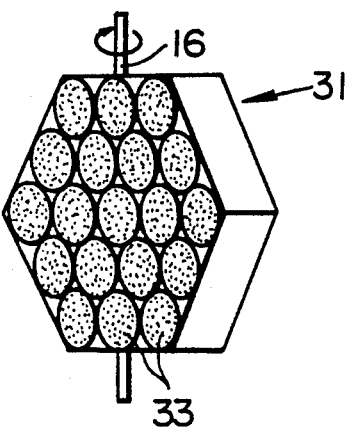

FIGS. 6 and 7 show the shapes of other diaphragms.

As shown in FIGS. 6 and 7, diaphragm 31, made of metal, or other suitable material, made up of a hexagonal plate or short hexagonal pillars provided with many short small diameter cylindrical through holes 32, open to pass light and closely arranged to maximize the quantity of passing light. The side wall of the cylindrical through hole 32 form a shading portion 33. Both the through hole 32 and its surrounding shading portion 33 form a small diaphragm unit. At two opposing points, passing through the center of the unit, and on the outer periphery of the diaphragm 31, shafts 16 are installed for rotation by motor 17, as shown in FIG. 5. When diaphragm 31 is in the normal state, i.e. no rotation, the face of the hexagonal plate is at right angles to the optical axis and, as shown in FIG. 7 (a), the front view, as seen from the optical axis direction, shows the opened state where the largest quantity of light passes through through holes 32.

When the level of the dimmer signal becomes rather high, the diaphragm 31 is turned accordingly, and the light is shielded to a considerable extent by the shading portions 33, as shown in FIG. 6. When the level of the dimmer signal is extremely high, the diaphragm 31 is further turned and, as shown in FIG. 7 (b), the diaphragm 31 is further turned to an angle at which the passing beam becomes almost zero.

Although the aforementioned diaphragm devices are used in the light source device which uses a white color source for color imaging, the diaphragm devices can also be used in the light source device which forms a color face sequential type illuminating means. For example, FIG. 8 shows an embodiment wherein the diaphragm of the first embodiment is used for an endoscope having the color face sequential type light source device.

Figure 8:
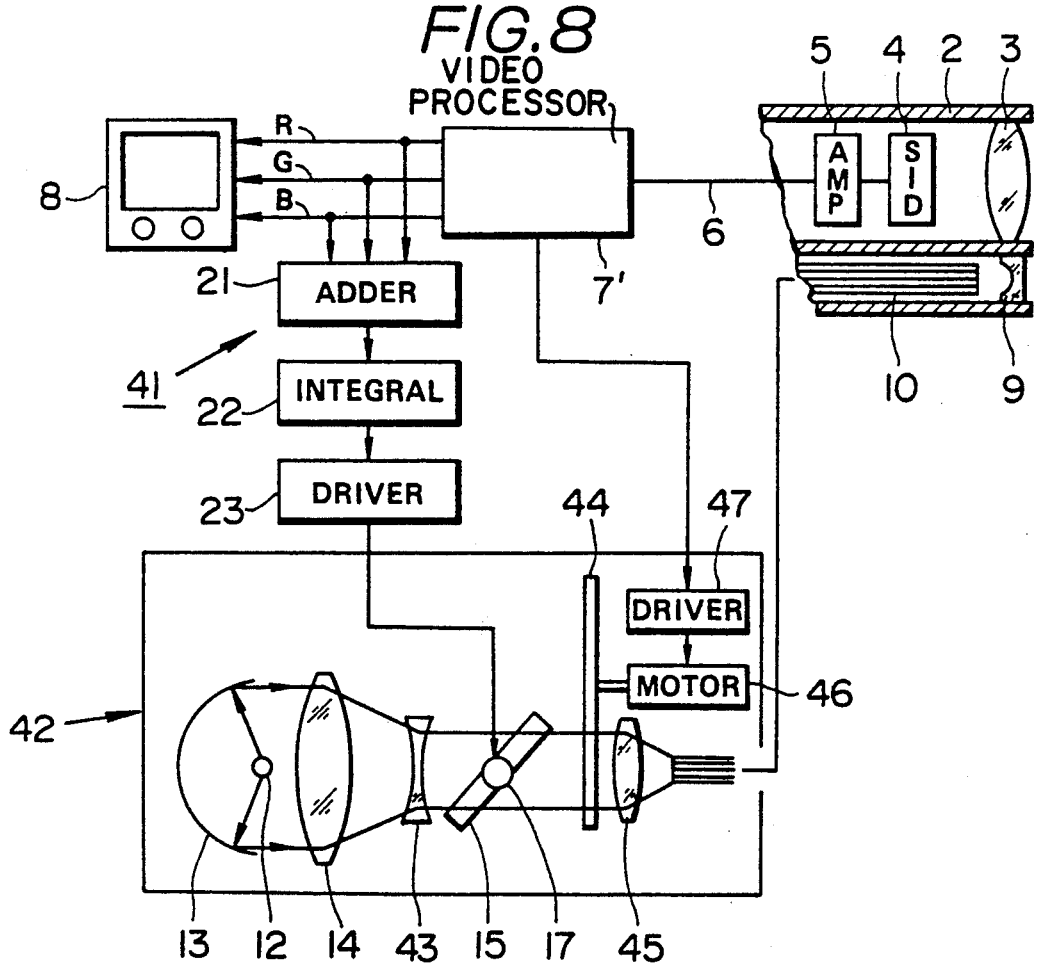

This endoscope 41 of FIG. 8 uses a monochrome solid state image pick-up device 4 which is not equipped with the color filter, such as mosaic-arranged filter. In the light source device 42, the beam condensed by condenser 14 located near the concave reflecting mirror 13 is made into parallel beam by a concave lens 43 which is smaller in diameter than condenser 14. Midway of the parallel beam the diaphragm 15 of the first embodiment is arranged and a rotary (color) filter 44 is arranged adjacent to diaphragm 15. The beam passing through the rotary filter 44 is condensed again by a small diameter condenser 45 and irradiated onto the end face of the light guide 10.

Rotary filter 44 has fan-shaped red transmission filter, green transmission filter and blue transmission filter arranged around the rotating center driven by motor 46. Motor 46 is driven by pulse signals supplied from motor driving circuit 47. The color transmission filters are sequentially placed in the optical path.

The subject is illuminated through the color transmission filters. The light reflected from the subject, illuminated by each color, is received by the light receiving elements of the solid state image pick-up device and, after the read-out signal is applied, taken into the video processor 7'. The signals taken into the video processor 7' and A/D converted are sequentially stored in color frame memories (not illustrated) for color recording through a switching circuit (not illustrated). The signal data, stored in the three color frame memories, are simultaneously read, D/A converted and into analog signals, amplified by a color amplifying circuit (not illustrated) and made into color signals R, G and B and then input to color television set 8.

Unlike the optical system shown in FIG. 3, the light source device 42 uses concave lens 43 to reduce the area of the parallel beam so that a rotary filter 44, of smaller area, can be used. The rotary filter 44 can be made of heat-resistant interference filter.

Other configurations of the endoscope, as shown in FIG. 3, can be made.

The diaphragm can be arranged between the reflecting mirror 13 and condenser 14.

The diaphragm are not limited to devices in which the diaphragm 15 or 31 is driven by the motor 17 in accordance with the dimmer signal, but also includes devices in which the diaphragm 15 or 31 is manually driven.

Figure 9:
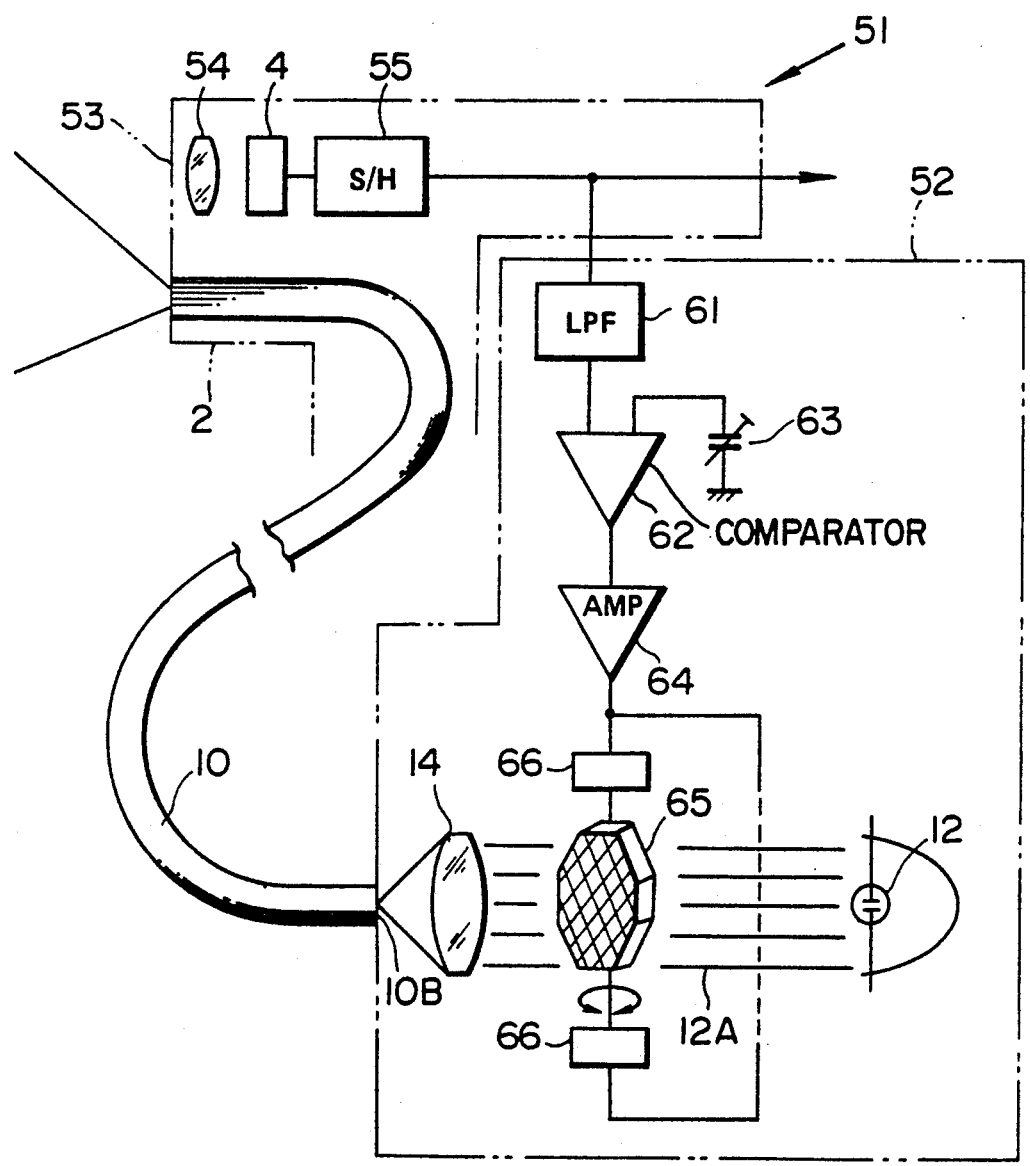
FIG. 9 is simplified block diagram for explaining an endoscope including the sample-hold circuit and the diaphragm device and control system of the present invention.

FIG. 9 shows diagrammatically the electronic endoscope equipped with the a sample-held circuit of the present invention in which the various of the diaphragm devices described herein may be utilized.

In FIG. 9, light inlet end face 10B of light guide 10 of endoscope 51 is connected to the light source device 52. Endoscope 51 has the end of light guide 10 arranged at the end face of the inserting part 2 of the endoscope and the solid state image pick-up device 4 facing the observation window 53. Solid state image pick-up device 4 consists of CCD, etc. which convert a picture image, formed on its imaging surface through the observations window 53 and optical imaging system (object optical system) 54, into electrical signals. The picture image signals obtained by solid state image pick-up device 4 are input to a video processor, such as the processor 7, 7' of FIGS. 3 and 8 through the sample holding circuit 55 provided in the endoscope 51, and transferred to low-pass filter 61 provided in the light source device 52. The output end of low-pass filter 61 is connected to one input end of comparator 62. To the other input end of the comparator 62, a variable reference voltage source 63 is connected. The output end of the comparator 62 is connected to galvanometer 66 for driving diaphragm 65 of the diaphragm device to be described later via the amplifier 64.

The video discrete value signals, obtained from the solid state image pick-up device 4, are sample-held by sample holding circuit 55 and then integrated for several frames by low-pass filter circuit 61. The average light quantity signal, during that time, is obtained. The signal is compared with the reference voltage of the reference voltage source 63, set to correspond to the set quantity of light. The difference is amplified and used to drive galvanometer 66 which turns the diaphragm 65 to control the reducing angle. This series of operating systems automatically controls the brightness of the illuminating light, thereby adjusting the brightness of the picture image properly. The picture image is observed on a monitor such as shown at 8, FIGS. 3 and 8.

The aforementioned diaphragm 65 of the diaphragm device is arranged in the outgoing optical path 12A of the illuminating light fired from light source lamp 12 of the light source device. The light transmitted through the diaphragm is condensed by the condenser 14 into light inlet end face 10B of the light guide 10.

Specific configuration of the aforementioned diaphragm device will be explained.

Figure 10:
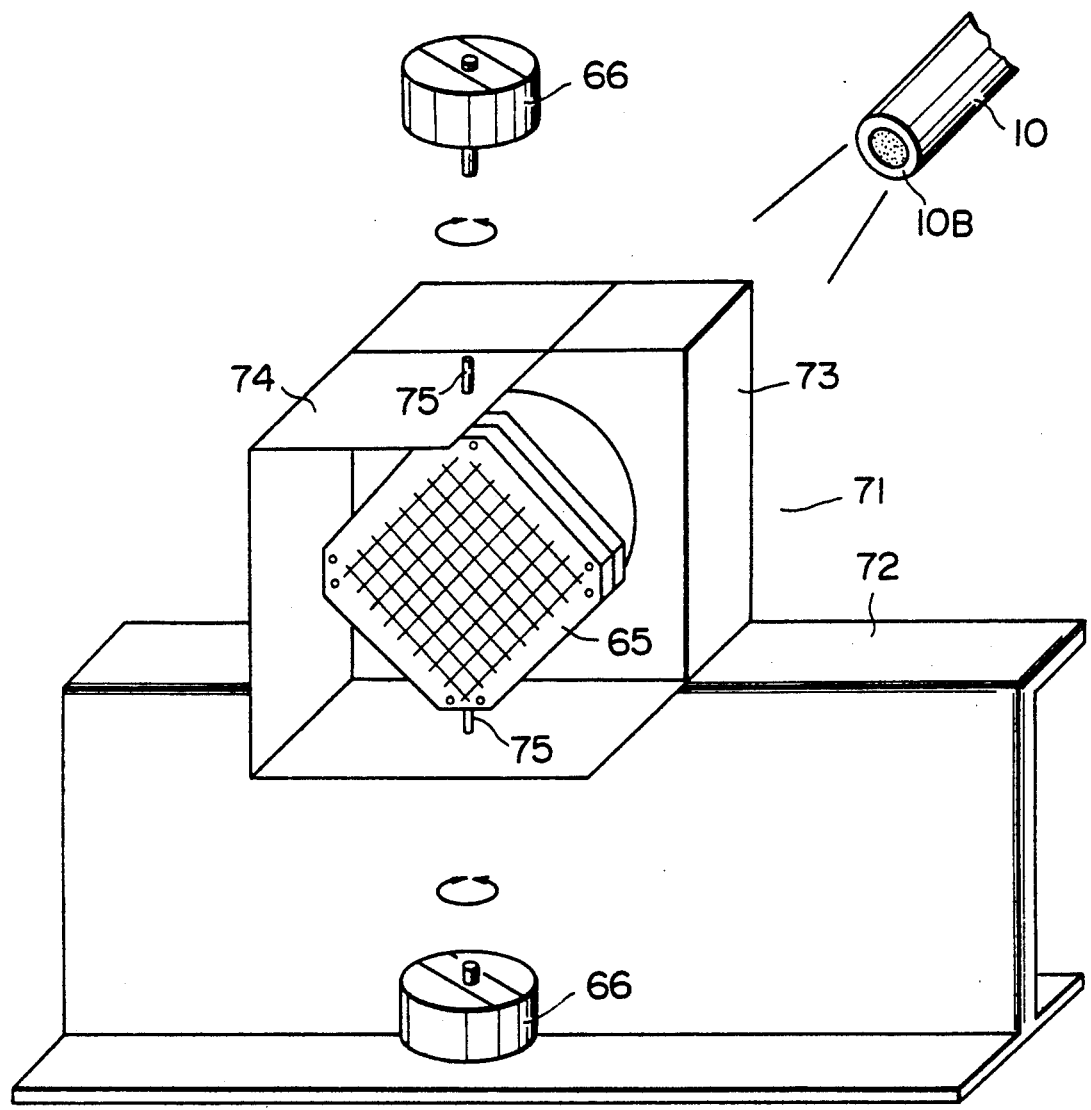
FIG. 10 is a perspective view showing main parts of the diaphragm device of FIG. 9.
Figure 11:
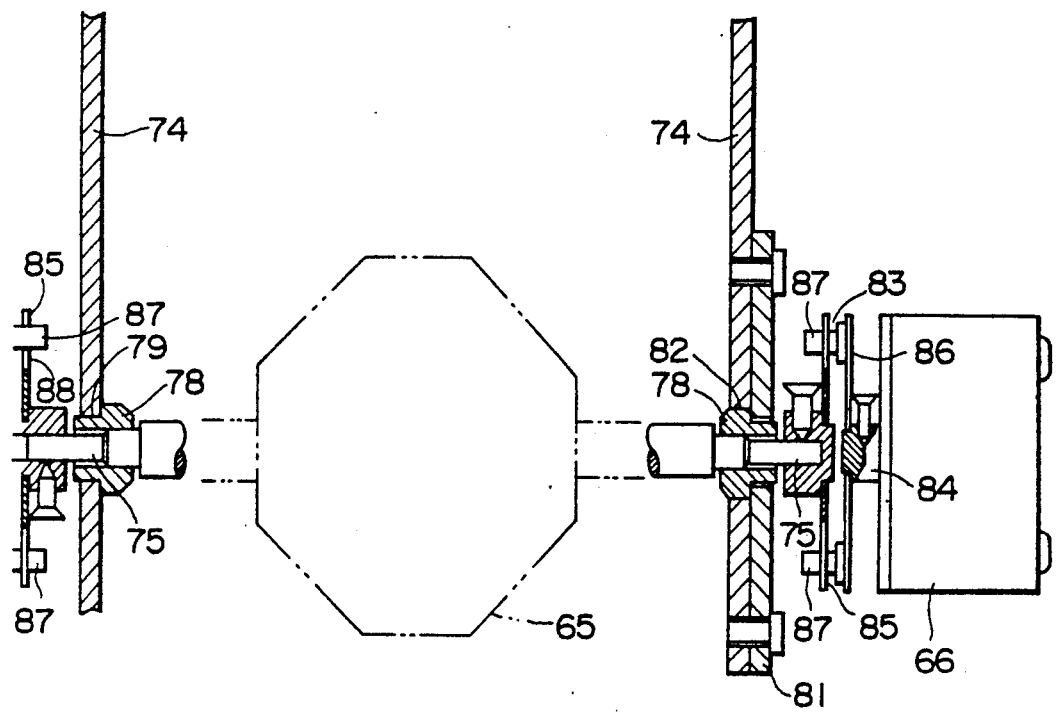
FIG. 11 is a side sectional view of the diaphragm device of FIG. 10.
Figure 12:
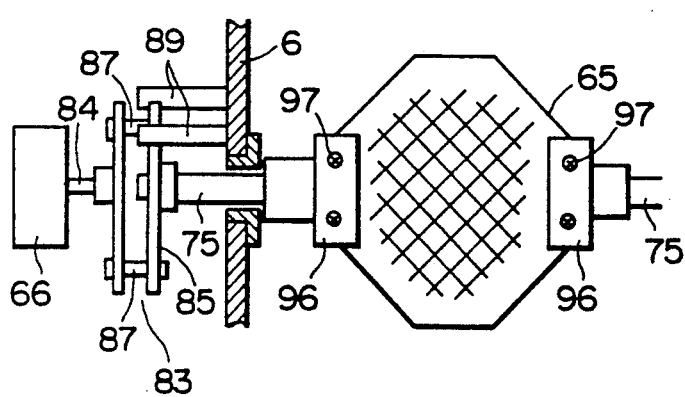
FIG. 12 is a sectional view of the joint portion of the diaphragm device of FIG. 10.
Figure 13:
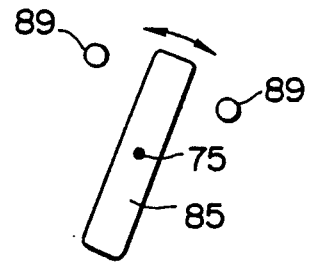
FIG. 13 is a front view of the inclination limiting mechanism of FIG. 12.

FIG. 10 shows a dimmer section 71 including the diaphragm device which is installed on mount 72. Lens frame 73, for installing the condenser 14, and bearing supporting member 74 are installed on mount 72. Diaphragm 65, to be detailed late, is provided with rotating shafts 75 at both ends. Rotating shafts 75 are supported by bearings 78 installed on bearing supporting member 74 as shown in FIG. 11. One bearing 78 is fixed in mounting hole 79 formed in bearing supporting member 74 while the other bearing 78 is mounted in another supporting plate 81. In the bearing supporting member 76, on the supporting plate 81 side, a cut hole 82 is formed. Bearing 78 is inserted in cut hole 82 and supporting plate 81 is installed. The end of each rotating shaft 75, pierced through the bearing supporting member 74, is connected to driving shaft 84 of the aforementioned galvanometer 66 by joint 83. The aforementioned joint 83 has an arm 85 installed at the end of rotating shaft 75 and an arm 86 installed on driving shaft 84 of galvanometer 66. At the end of arm 86, pins 87 project. Slits 88 is formed in arm 85 through which pins 87 are inserted. Slits 88 in arm 85 are in the radiant direction. Even if the driving shaft 84 of galvanometer 66 and rotating shaft 75 are misaligned with each other, accurate rotation is made. Arm 85 installed at the end of rotating shaft 75 is limited in its rotating range. That is, as shown in FIGS. 12 and 13, arm 85 is moved between a pair of stoppers 89 projected from bearing supporting member 74. The moving range restricted between stoppers 89 is, preferably, 30°.

Figure 16:
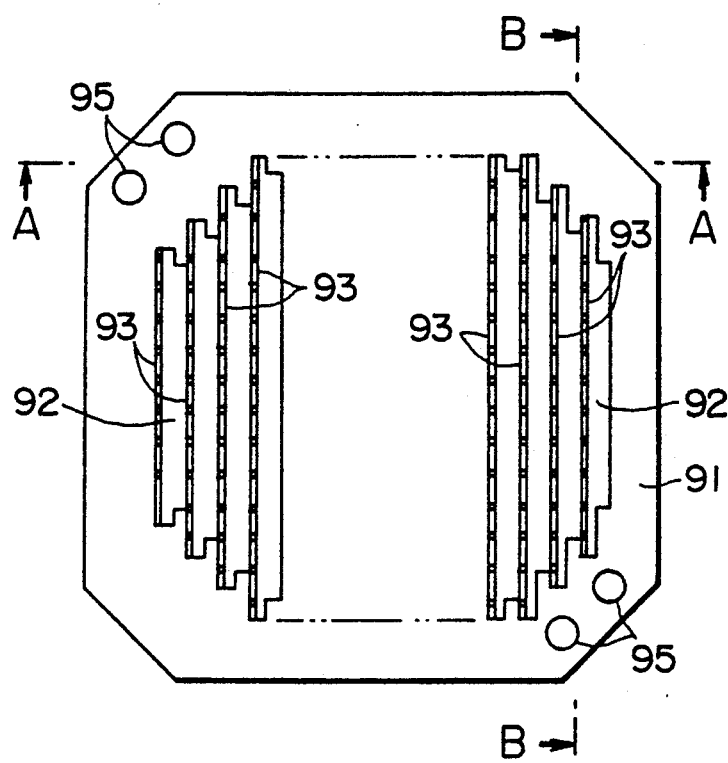
FIG. 16 is a front view of the diaphragm of FIG. 14.
Figure 17:
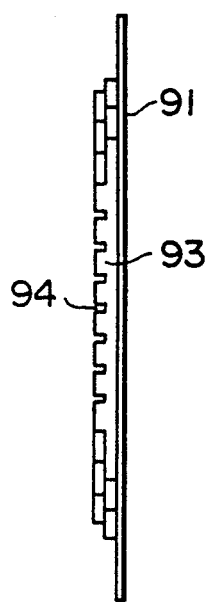
FIG. 17 is a side view of the diaphragm plate of FIG. 15.
Figure 18:
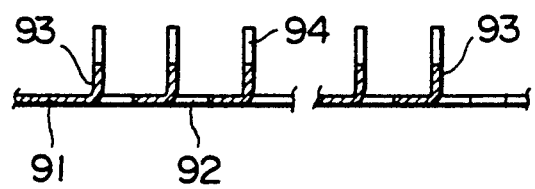
FIG. 18 is an enlarged sectional view along line A—A in FIG. 16.
Figure 19:
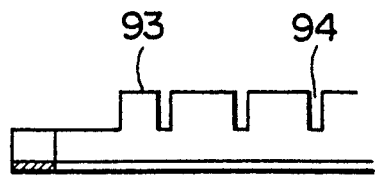
FIG. 19 is an enlarged sectional view along ling B—B of FIG. 16.
Figure 20:
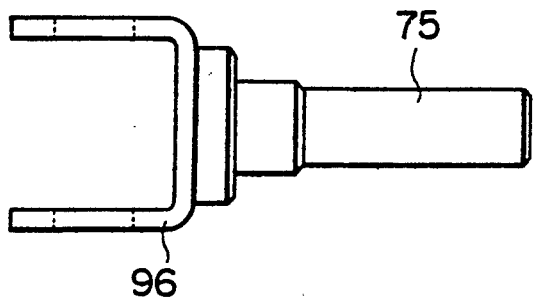
FIG. 20 is a side view of the rotating shaft of FIG. 20 portion.
Figure 21:
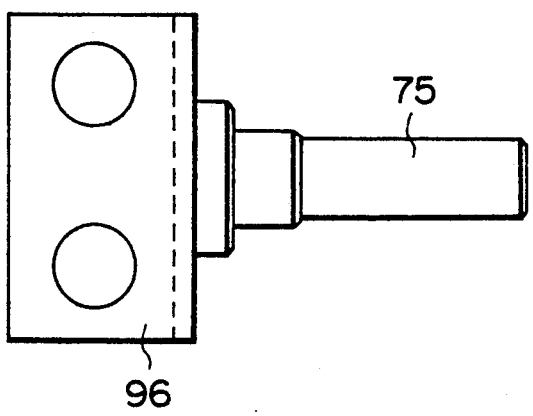
FIG. 21 is a plan of the rotating shaft of FIG. 20.

The aforementioned diaphragm 65 is formed, as shown in FIGS. 14–19, and consists of lamination of 4 almost square diaphragm plates 91. Each diaphragm plate 91 has many parallel narrow cut holes 92 along the mutually opposing sides. The remaining band-like are raised perpendicularly to the plate surface of the diaphragm 91 and form the light shading plates 93, as shown in FIGS. 16 to 18. The shading plates 93 are in parallel with one another and perpendicular to the plate surface of the diaphragm plate 91. When the plate surface of diaphragm plate 91 is placed at right angles to the optical axis of outgoing optical path 12A, thickness can be provided in the direction of the optical axis. There is a slit-like opening between the plate surfaces of shading plates 93 to pass illuminating light. Each shading plate 93 has engaging grooves 94 cut at set intervals of the shading plates 93. The engaging grooves of the shading plates 93 are arranged in a straight line. The depth of the engaging groove 94 is half the height of the shading plate 93. The diaphragm plate 91 is obliquely cut, at the four corners, at 45°. A opposite corners, interposing the center of the diaphragm plate 91, a pair of holes 95, for mounting screws, are drilled in plate 91. Two diaphragm plates 91 are put together by placing the shading plates 93 at right angle with one another with grooves 94 on the respective plates engaged. The remaining two diaphragm plates 91 are put together in the same manner. The two sets are further put together to appear as shown in FIG. 15. When so arranged, the shading plates 93 are perpendicular to one another and superposed, one upon another, as viewed from the front of diaphragm plate 91. At the corners, with the screws inserted in holes 95, the rotating shafts 75, shown in FIGS. 20 and 21, are installed. The rotating shaft 75 is provided with a U-shaped frame 96 for receiving the aforementioned corner part and is tightened and secured by mounting screws 97, inserted in holes 95 in frame 96. As shown in FIG. 14, the center of rotating shaft 75 crosses shading plates 93 at the angle of 45° and is at right angles to the rising direction of shading plates 93.

Diaphragm 65 set in the outgoing optical path 12A as above described, is turned by means of galvanometer 66 to select the reducing angle. The greater it is turned, the larger the reducing angle. When the reducing angle is zero, i.e. when the diaphragm 65 is at right angles to the optical axis of the outgoing optical path, shading plates 93 are in parallel with the optical axis. The illuminating light is only interrupted by the thickness of shading plates 93. Thus, the largest quantity of illuminating light is passed. The light transmissivity at that time is preferably more than 70%. When the reducing angle is increased, shading plates 93 are inclined and the plate surfaces gradually interrupts the illuminating light and decreases the quantity of illuminating light. The reducing effect is achieved generally by means of diaphragm 65. The entire outgoing optical path 12A is uniformly reduced. Since the illuminating light, reduced uniformly for the entire outgoing optical path 12A, is condensed by condenser 14 and is incident on the light inlet end face 10B of the light guide 10, various incident angles can be obtained regardless of the amount of reduction. For this reason, the firing angle from light guide 10 becomes large and a wide illuminating range can be obtained. Because the illuminating light is uniformly reduced for the entire outgoing optical path 21A, the spectral characteristic of each part in the illuminating range changes when the amount of reduction changes. Furthermore, because the shading plates 93 crossed one another, it is possible to increase the quantity of the transmitting light when the reducing angle is zero. Since the shading plates 93 cross the center axis of the rotating shaft 75 at 45°, the light transmitting hole portions become rhombuses and, because the holes increased or decreased in size, uniform reducing is obtained. Structurally, a small turn gives a big amount of reduction. Hence, the diaphragm can be made lighter and more compact.

The smaller the width of the slit, i.e. the opening surrounded by the square shading plates 93, the higher the uniformity of the light quantity. The larger the slit width, the larger the quantity of transmitting light when opened (no rotation). The smaller the slit width, the larger the volume of diaphragm 65.

In the aforementioned embodiment, with the diaphragm 91 of a thickness 0.15 mm, condenser 14 of a diameter of 30 mm and the reducing angle within 30°, the transmissivity, when opened, was 87.1% in the first manufacturing example, with the slit width 2 mm, diaphragm 65 thickness of 4.9 mm and number of grids about 150. In the second manufacturing example, with the slit width 4 mm, diaphragm 65 thickness of 9.8 mm and number of grids about 38, the transmissivity, when opened, was 93.6%

The aforementioned configuration is superior in transmissivity and weight (about 1/5 including the supporting parts to the lotus root type made up of a thick plate with many dulled holes).

Figure 22:
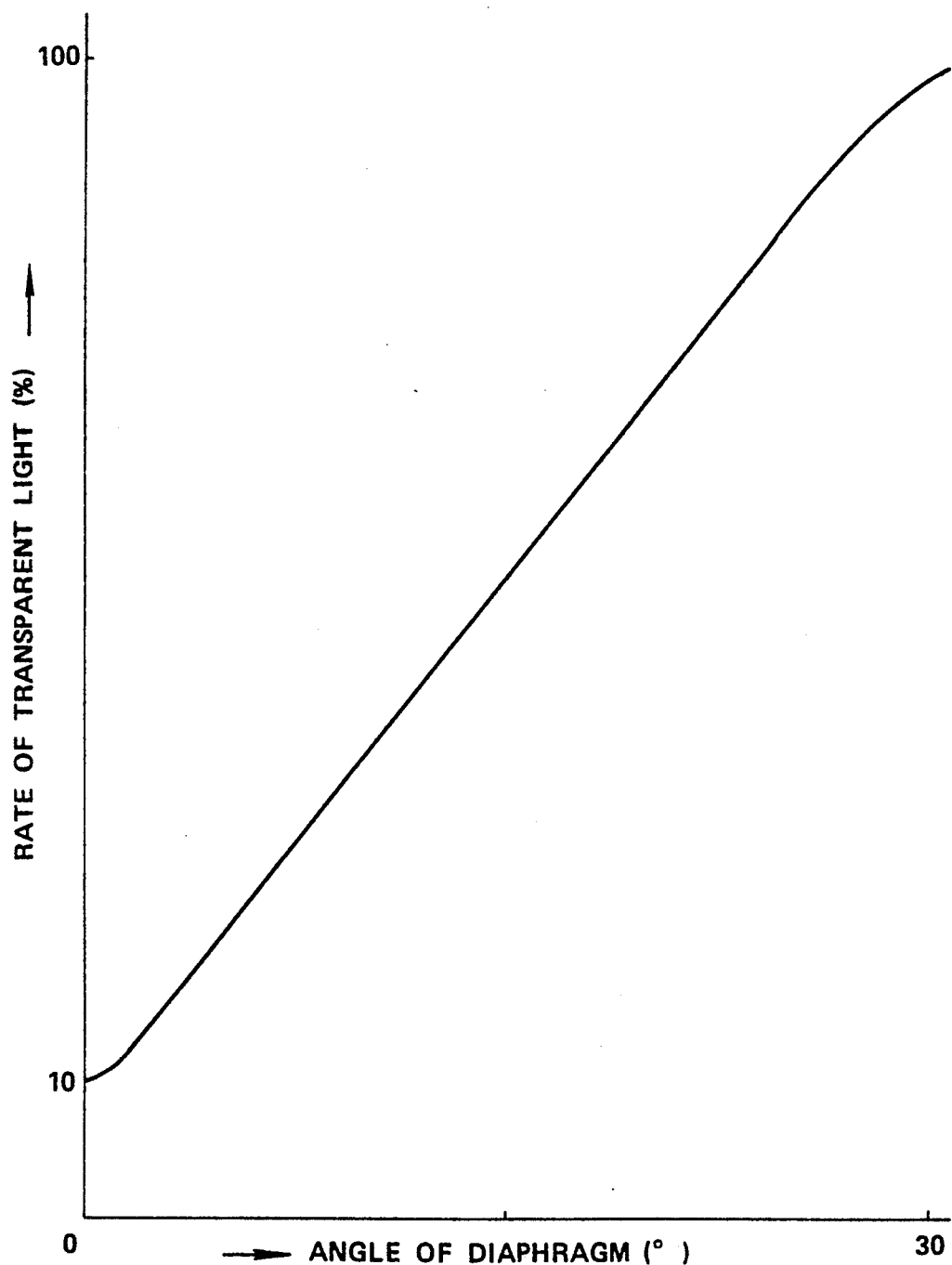
FIG. 22 is a graph showing characteristics of the diaphragm of FIG. 9.

FIG. 22 shows a relationship between the rotating angle of the diaphragm, i.e. angle of diaphragm, and the rate of transparent light. It shows that almost linear relationship is obtained. The rate of transparent light is obtained by subtracting the quantity of transmitted light from total quantity of light from the light source and dividing the difference by the total quantity of light from the light source.

Figure 23:
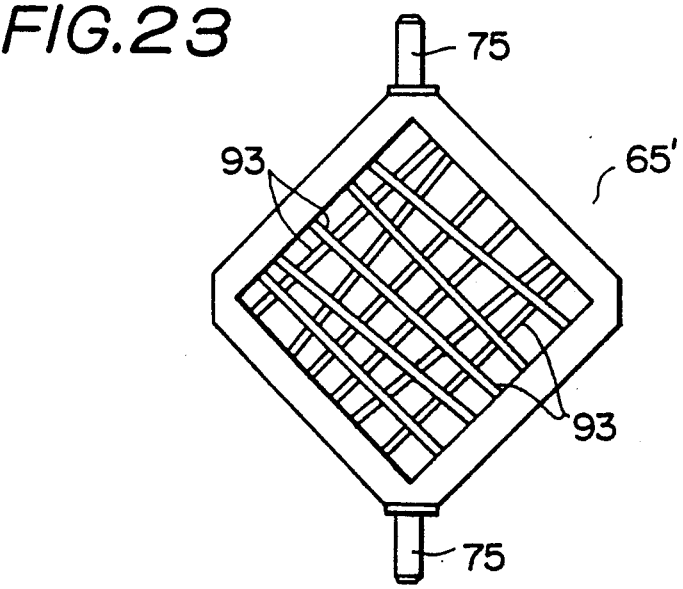
FIG. 23 is a front view of another diaphragm for use with the electronic endoscope of FIG. 9.

FIG. 23 shows a diaphragm 65' which might be used in the present invention. Diaphragm 65' has the shading plates 93 randomly crossed instead of crossing at right angles.

The present invention is not limited to the aforementioned diaphragms. For example, instead of cutting and raising the shading plates from the diaphragm plate, a separate shading plate can be installed in the frame of the diaphragm.

In order to decrease the angle of diaphragm further, another set of two diaphragm plates can be superimposed. The most desirable range of the rotating angle of the diaphragm is from about 15° to about 45°.

Figure 24:
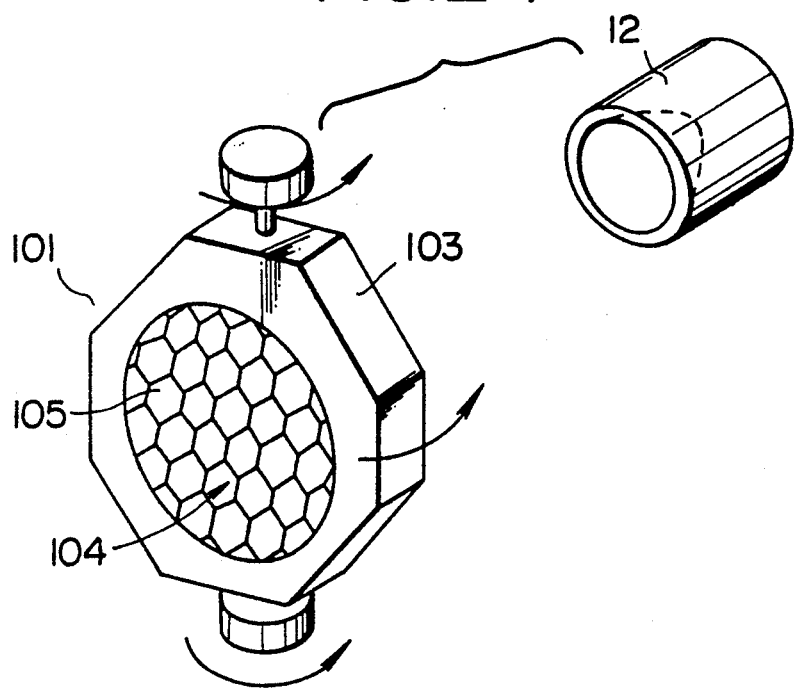
FIG. 24 is a perspective view showing still another diaphragm for use with the electronic endoscope of FIG. 9.

FIG. 24 shows a diaphragm 101 which might also be used in the present invention.

Figure 25:
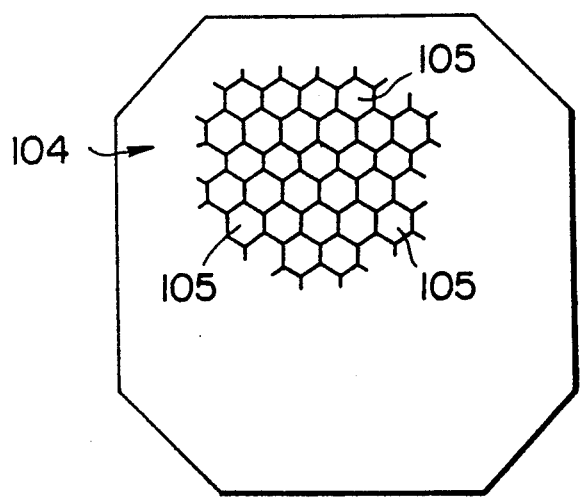
FIG. 25 is a front view of a honeycomb construction of FIG. 24.
Figure 26:
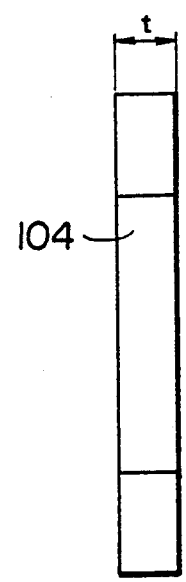
FIG. 26 is a side view of the honeycomb construction of FIG. 25.

In such diaphragm 101 is arranged at the position of the diaphragm 65 in the outgoing optical path 12A of the light source lamp 12 shown in FIG. 9 and has a honeycomb structure 104 held in the holding frame 103. As shown in FIGS. 25 and 26, the honeycomb structure 104 is formed in a plate-like shape which has a relatively large thickness and many honeycomb holes 105 with the axis oriented in the thickness direction. Honeycomb structure 104 is cut obliquely at the four corners. Holes 105 of the honey comb structure 104 are formed by bending thin aluminum band-like plates and sticking the plate together. This can be done by applying adhesive at the sticking points, placing the band-like plates, one upon another, and crimping the plate edges, or in any other attaching manner. It is possible to use very thin materials making the structure light in weight.

As shown in FIGS. 27 and 28, the holding frame 103 consists of a plate body 107 having a circular transmission opening 106, and at the top, bottom and left end and standing parts 108. Standing parts 108 are bent inward at the end to form the holding spaces 109 as shown in FIG. 28. In the holding spaces 109, the edge part of the honeycomb structure 104 is fit and in the inserting holes 110 formed in the holding parts 109, set pins (not illustrated) are inserted to fix the honeycomb structure 104.

At both the top and bottom ends of holding frame 103, rotating shafts 111, 111, supported by bearings, (not illustrated) are installed. The rotating shafts are connected to the aforementioned galvanometers 66 and turned by means of the galvanometers 66 which are driven by output of the amplifier 64 shown in FIG. 9.

Diaphragm 101, thus formed, has honeycomb holes 105 whose axis direction is parallel with the optical axis of the outgoing optical path 12A. When diaphragm 101 is inclined, the axis direction of the honeycombs 105 is inclined against the optical axis.

When the diaphragm 101 is not inclined, the axis direction of the honeycomb holes 105 is in conformity with the direction of the optical axis of the outgoing optical path 12A. That is, all the hole diameters of the honeycomb holes 105 are contributing to the transmission of the light. What interrupts the light at that time is only the thin thickness of the material. Therefore, a big quantity of transmitting light is obtained.

To reduce the quantity of transmitting light, the diaphragm 101 is inclined by the galvanometer 66 and the axis direction of the honeycombs 105 is inclined against the direction of the optical axis of the outgoing optical path 12A. Thus, the transmission hole diameter of the honeycomb holes 105 is decreased and reduces the quantity of transmitting light.

Since reduction is made through the honeycomb holes 105 of the honeycomb structure 104, the quantity of light is uniformly reduced for the entire area of the outgoing optical path 12A. Because the illuminating light uniformly reduced for the entire outgoing optical path 12A is condensed by the condenser 14 and is incident on the light inlet end face 10B of the light guide 10, various angles of incidence can be obtained regardless of the amount of reduction. For this reason, the firing angle from the light guide 10 is increased and a wide illuminating range can be obtained. In addition, any particular wavelength is not cut when the angle of incidence changes. The spectral characteristic is also good. Since the aforementioned honeycomb structure can be made light in weight, it can be swiftly set at an amount of reduction suitable for observation by controlling the reducing amount of the diaphragm 101 on basis of the output of the solid state image pick-up device 4.

Figure 30:
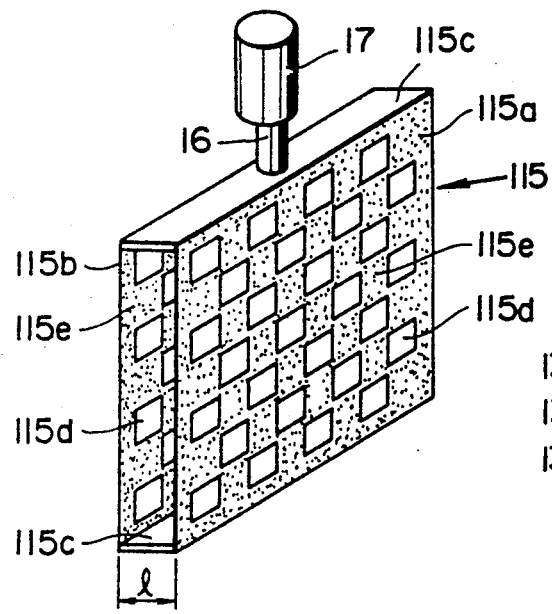
FIG. 30 is a perspective view showing a further diaphragm for use with the electronic endoscope of FIG. 9.

FIG. 29 shows still a further diaphragm device useful in the present invention. As shown in FIG. 30, diaphragm 115 has two shading plates 115a and 115b opposed to each other via the spacers 115c installed at the top and bottom.

The shading plates 115a and 115b are made of metal with the surfaces black-processed. The distance 1 between plates 115a and 115b is fixed by spacer 115c.

In the shading plates 115a and 115b, a plurality of light transmitting holes 115d, of small area, are regularly punched in checker pattern. The light transmitting holes 115d, in the shading plates 115a and 115b, are opposed to each other. Between adjoining light transmitting holes 115d on the shading plates 115a and 115b, shading parts 115e are formed.

At the center of the upper spacer 115c, installed between the shading plates 115a and 115b, shaft 16 is fixed. Shaft 16 is connected to motor 17.

If the diaphragm 115 is turned and inclined, as shown in FIG. 29, from the normal state, i.e. the state in which the shading plates 115a and 115b are right angles to the optical axis, the light hitting the shading parts 115e is interrupted and the quantity of light to go toward the condenser 14 is reduced almost uniformly for all the diaphragm units.

Figures 31A, 31B:
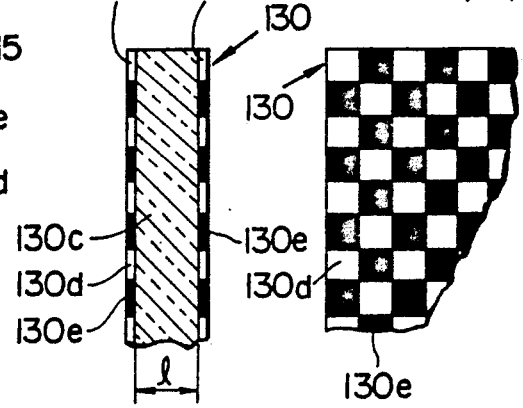
FIG. 31 (a) shows a still further for use with the endoscope diaphragm of the present invention in front view and 31 (b) is a side view of the diaphragm of FIG. 31 (a)

FIG. 31 shows another diaphragm useful in the present invention. In this illustration, diaphragm 130 consists of a transparent plate 130c with a specified thickness of 1 and opaque thin film sheets 130a and 130b attached to both sides of transparent plate 130c.

In the thin film sheets 130a and 130b, light transmitting holes 130d, with small area, are provided in checker pattern at the corresponding positions on both sheets. Between the light transmitting holes 130a and 130d, shading portions 130e are formed. The shading portions 130e can be directly formed on the surface of the transparent plate 130c by printing or by other means.

If the diaphragm 130 is turned to a specified angle by a motor, the quantity of light transmitting the light transmitting holes 130e is controlled in accordance with the rotating angle, as in the case of the aforementioned sixth embodiment, and the effect is almost the same as that of the sixth embodiment.

Figure 32A:
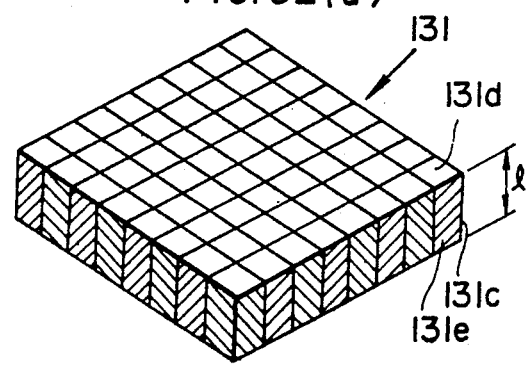
FIG. 32 (a) is a perspective view of still another diaphragm for use with the electronic endoscope of FIG. 9 and FIG. 32 (b) a perspective view showing the diaphragm unit.
Figure 32B:
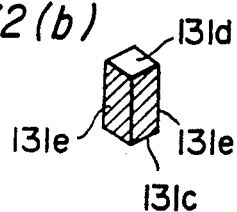

The diaphragm 131 also useful in the present invention and shown in FIG. 32, is formed by assembling, for example, many rectangular parallel piped transparent unit blocks 131c. On the peripheral side surfaces of the unit blocks 131c, shading parts 131e are formed by printing or other means. The top and bottom of the unit block 131c are the light transmitting parts 131d.

In diaphragm 131, formed by bonding a plurality of the unit blocks 131c, the mutually adjoining light transmitting parts 131d are partitioned by shading parts 131e.

When the diaphragm 131 is in a normal state, i.e. when it is not turned, the light transmitting parts 131d are faced with the optical axis, i.e. the opened state exists when the largest quantity of light is passed.

Figure 33:
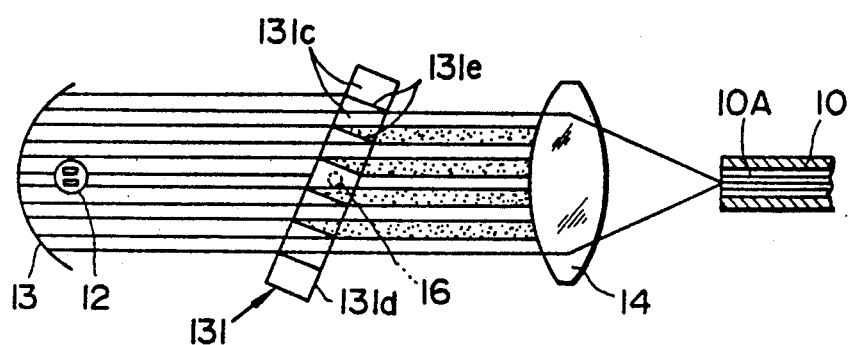
FIG. 33 is an explanatory drawing showing the diaphragm device of FIGS. 32 (a), 32 (b)

As the level of the dimmer signal becomes gradually high, diaphragm 131 is turned in accordance with the level, and as shown in FIG. 33, the beam incident on the diaphragm 131 is interrupted by the shading parts 131e. Thus, the quantity of the light passing through the diaphragm 131 is reduced. The light transmitting parts 131d are not limited to the rectangular parallel piped and can be regular triangle column, regular pentagon column or regular hexagon column. It is generally also possible to use columnar transparent bodies, e.g. cylindrical transparent bodies and to form the diaphragm units by gaps between the cylinders.

Figure 34:
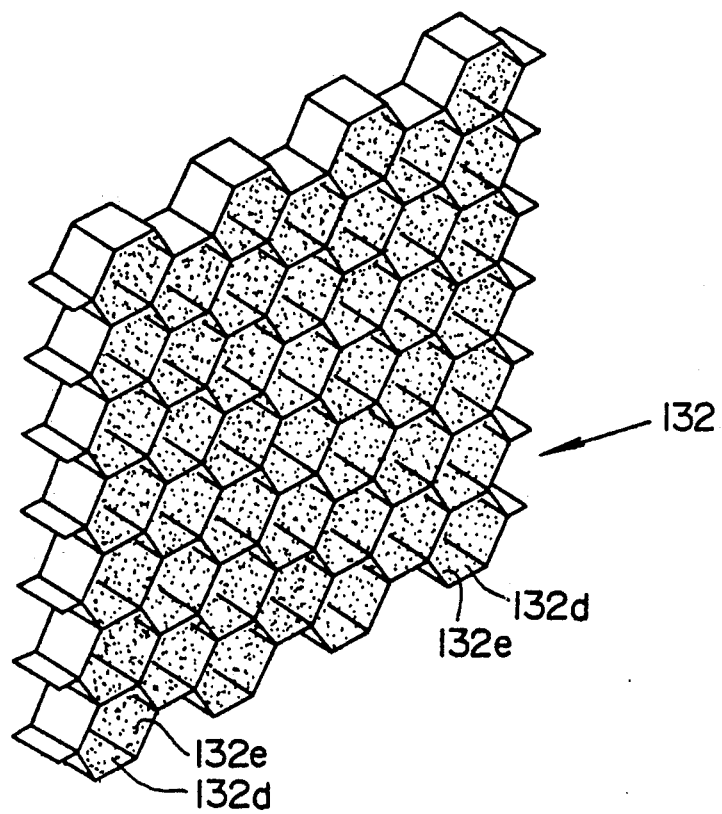
FIG. 34 is a perspective view of a still further diaphragm for use in the present invention.

The light transmitting parts 132d of the diaphragm 132 useful in the practice of the present invention and shown in FIG. 34, are honeycomb-like holes and the inner periphery surfaces form the shading parts 132e. When diaphragm 132 is turned at a specified angle, the shading parts 132e interrupt the beam from the light source 12, as in the case of the aforementioned seventh embodiment, and the quantity of light is reduced.

Figure 35:
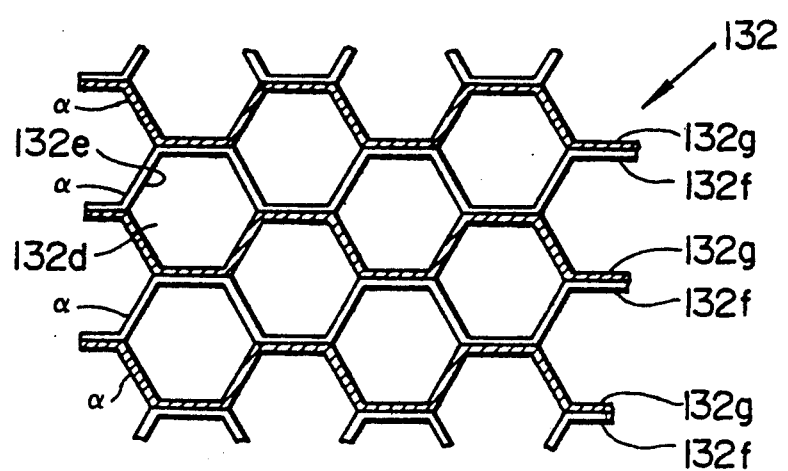
FIG. 35 a front view of the diaphragm of FIG. 34.

As shown in FIG. 35, the diaphragm 132 is made by forming on flat plate a wave pattern 132f and forming another flat plates a reversed wave pattern 132g and by adhesively sticking or abutting the mutual contacting surfaces. As a specific means to form this honeycomb, firstly the flat plates 132f and 143g are piled one upon another in multiple layers. The upper surface of one flat plate 132f and the under surface of the other flat plate 132g are bonded together at a fixed intervals and at a fixed width. Then the under surface of the flat plate 132f and the upper surface of another flat plate 132g are bonded at a fixed width.

In order to make the light transmitting parts 132d into regular hexagon, as shown in FIG. 35, the bonding parts and non-bonding parts of the flat plates 132f and 132g are made almost equal in width. The laminated flat plates 132f and 132g are pulled in the upper and lower direction as in the FIG. 35. Then only the non-bonded parts (indicated by α in FIG. 35) are bent to form the honeycomb.

With regard to the present invention, it is clear that various embodiments in a wide range can be formed on basis of the present invention without departing from the spirit and scope of the present invention. The present invention is not restricted by any particular embodiments except by the accompanying claims.

We claim:

1. An electronic endoscope comprising:
   an elongated insertable part;
   a light emitting means for emitting an illuminating light from the tip side of said insertable part;
   an objective lens, provided on the tip side of said insertable part, for forming an image from the area illuminated by said emitted light;
   a solid state imaging device, whose light receiving plane is on an image forming position of said objective lens, for forming an output signal from said formed image; and
   a sample-holding circuit, provided within said electronic endoscope, for sample-holding an output signal from said solid state image device.

2. An electronic endoscope according to claim 1, wherein said sample-holding circuit is on the tip side of said insertable part.

3. An electronic endoscope apparatus comprising:
   an electronic endoscope comprising an elongated insertable part, a light guide extended through said insertable part for emitting an illuminating light supplied to one end from the other end, an objective lens on the tip side of said insertable part for forming an image, a solid state image device having a light receiving plane in an image forming position of said objective lens and a sample-holding circuit for sample-holding an output signal from said solid state imaging;
   a light source unit for emitting an illuminating light beam toward one end of said light guide;
   an iris device, provided within said light source unit, for variably controlling the amount of illuminating light supplied to one end of said light guide based on an output of said sample-hold circuit;
   a video signal processing means for generating a standard video signal from an output signal of said sample-holding circuit; and
   a color monitor for displaying an output signal of said video signal processing means.

4. An electronic endoscope apparatus according to claim 3, wherein said iris device is a diaphragm device in said light beam emitted from said light source, said diaphragm device consisting of a diaphragm assembly made up of a plurality of diaphragm units each having light transmitting area and a shaded part surrounding said light transmitting area, said diaphragm assembly having a cross-sectional area exceeding the cross-sectional area of said light beam emitted from said light source, means for supporting said diaphragm assembly for rotation about an axis substantially perpendicular to the axis of said light beam from a point where the light transmitting axis of said diaphragm units and the axis of said light beam are parallel to a point where said light transmitting axis of said diaphragm units and the axis of said light beam are oblique and said light beam from said light source is at least partially intercepted by the shaded parts surrounding the light transmitting parts and means for rotating said diaphragm assembly on said perpendicular axis for adjusting said light transmitting axis of said diaphragm units relative to said axis of said light beam for regulating the light from said light source transmitted through said diaphragm assembly, and condenser means for receiving the light transmitted through said diaphragm assembly and for condensing and transmitting condensed light.

5. A diaphragm device, as claimed in claim 4, in which said diaphragm assembly consists of a light shading plate with a proper thickness provided with many through holes with small sectional area perpendicularly to the plate surface.

6. A diaphragm device, as claimed in claim 5, in which said through holes are closely formed in two directions.

7. A diaphragm device, as claimed in claim 4, in which said diaphragm assembly is in square grid frame form.

8. A diaphragm device, as claimed in claim 4, in which said diaphragm assembly is in regular hexagon grid frame form.

9. A diaphragm device, as claimed in claim 4, in which said diaphragm units are pillar-like transparent bodies provided with light shading films on the side surface.

10. A diaphragm device, as claimed in claim 4, in which said diaphragm assembly consists of a pair of plate-like members each having regularly arranged light transmitting areas surrounded by shaded parts and whose light transmitting areas are faced, one with the other, on said plate-like members and means for supporting said plate-like members for rotating in the light beam of said light source for regulating the light transmittal therethrough.

11. A diaphragm device, as claimed in claim 4, in which said diaphragm assembly consists of a light transmitting transparent plate having light transmitting portions and shading parts arranged in checker pattern on both sides and means for supporting said plate for rotation about an axis parallel with the plate surface.

12. A diaphragm device, as claimed in claim 4, which includes a driving means for rotating said diaphragm assembly, an imaging optical system and said endoscope, said imaging optical system having a focal plane, a solid state image pick-up device at said focal plane of said imaging optical system and means for controlling said driving means in response to the brightness level at said sample-holding circuit.

* * * * *